US009919991B1

(12) United States Patent
Lekos et al.

(10) Patent No.: US 9,919,991 B1
(45) Date of Patent: Mar. 20, 2018

(54) SYSTEMS AND METHODS FOR PURIFICATION OF GLYCERIN (71) Applicant: Whole Energy Fuels Corporation, Bellingham, WA (US)

(72) Inventors: Orion Lekos, Bellingham, WA (US); Atul Deshmane, Bellingham, WA (US)

(73) Assignee: Whole Energy Fuels Corporation, Bellingham, WA (US)

( * ) Notice: Subject to any disclaimer, the term of this patent is extended or adjusted under 35 U.S.C. 154(b) by 481 days.

(21) Appl. No.: 14/540,400

(22) Filed: Nov. 13, 2014

Related U.S. Application Data

(60) Provisional application No. 61/903,756, filed on Nov. 13, 2013.

(51) Int. Cl.
*C07C 29/80* (2006.01)
*C07C 29/76* (2006.01)
*B01D 3/02* (2006.01)
*B01D 3/00* (2006.01)
*C07C 29/74* (2006.01)

(52) U.S. Cl.
CPC .............. *C07C 29/80* (2013.01); *B01D 3/007* (2013.01); *B01D 3/02* (2013.01); *C07C 29/76* (2013.01)

(58) Field of Classification Search
CPC .......... B01D 3/007; B01D 3/02; C07C 29/74; C07C 29/76; C07C 29/80
See application file for complete search history.

(56) References Cited

U.S. PATENT DOCUMENTS

| 2,234,400 | A | 3/1941 | Van et al. |
| 2,615,924 | A | 10/1952 | Reents |
| 2,741,638 | A | 4/1956 | James et al. |
| 2,772,207 | A | 11/1956 | Frankel et al. |
| 4,655,879 | A | 4/1987 | Brockmann et al. |
| 5,810,976 | A * | 9/1998 | Keith ............. B01D 3/10 159/24.1 |
| 7,126,032 | B1 | 10/2006 | Aiken |
| 2009/0198088 | A1* | 8/2009 | Tirio .............. B01D 15/185 568/870 |
| 2014/0008208 | A1* | 1/2014 | Pichach ........... B01D 3/38 203/1 |

OTHER PUBLICATIONS

Journey to Forever, "Glycerin", http://web.archive.org/web/20120118112100/http://www.journeytoforever.org/biodiesel_glycerin.html, Nov. 2010-Jan. 2012, 13 pages.

* cited by examiner

*Primary Examiner* — Brian A McCaig
(74) *Attorney, Agent, or Firm* — Michael R. Schacht; Schacht Law Office, Inc.

(57) ABSTRACT

A glycerin recovery system uses a reboiler and a heat exchanging system. The reboiler heats crude glycerin to separate the crude glycerin into finished glycerin and condensates such that the finished glycerin is in a range of 80-98% purity. The heat exchanging system transfers heat energy in the finished glycerin to the crude glycerin.

15 Claims, 6 Drawing Sheets

SYSTEMS AND METHODS FOR PURIFICATION OF GLYCERIN

RELATED APPLICATION

This application claims benefit of U.S. Provisional Application Ser. No. 61/903,756 filed Nov. 13, 2013, which is incorporated by reference herein in its entirety.

TECHNICAL FIELD

The present invention relates to the field of recycling and purification of organic effluents recovered from the biodiesel production process. More particularly, the present invention relates to the purification of glycerin and alcohols from a process for the manufacture of fatty acid alkyl esters.

BACKGROUND

Traditionally glycerin has been refined to make a 99.9% pure product for the USP market. The source for the glycerin came from either soap manufacturers or fat splitting. As biodiesel refineries started to come on line in the beginning of 2000, a new grade of crude glycerin started to become available. This product was around 50-80% pure and there was little to no market for it and it was considered a waste product of the biodiesel industry. Some larger refiners of biodiesel began to hire olechemical process engineering firms to design systems to upgrade the crude glycerin to a 99.9% pure product, but the expense of such systems would cost millions of dollars. This high cost of building a glycerin refinery resulted in only a few large scale refineries implementing glycerin refining into their production process. In order for smaller scale refineries below 100,000,000 gallons per year of biodiesel to consider building a glycerin refinery there needed to be a system that costs less and did not take up a large section of space since most refineries where utilizing most of their square feet for their production process. Also a new market needed to be developed that did not require a 99.9% pure glycerin. A technical market that could accept an 85-95% pure glycerin needed to be developed. Also a limiting factor was that it is more difficult to refine crude glycerin from biodiesel into 99.9% pure glycerin because of the unique contaminants that are present with the biodiesel based crude glycerin.

The crude glycerin from biodiesel is made as a coproduct from the transesterification of triglycerides into fatty acid alkyl esters. The three fatty acids are separated from the triglyceride leaving a glycerin molecule. This glycerin binds with residual sodium hydroxide or potassium hydroxide catalyst from the transesterification reaction and it also binds fatty acids that were attached to the sodium or potassium ion from the catalyst in the form of soaps. Any water that was in the triglycerides or water created from mixing up the catalyst also goes into the glycerin layer. Some partially reacted biodiesel and even some fully reacted biodiesel are also mixed with the glycerin as well as glycerides and finally 60% of the excess alcohol used in the transesterification reaction also mixes into the glycerin product. The result is a crude glycerin with fatty acids, mono- and di-glycerides, salts, soaps, alcohol, water, and some biodiesel. This creates a glycerin with around 50% purity.

There is public knowledge on the basic principles of purifying the crude glycerin from the biodiesel reaction. As discussed in the www.journeytoforever.org website under glycerin separation, glycerin is purified by adding phosphoric acid until the glycerin is neutral pH. It then splits into 3 layers. The top layer being fatty acids and biodiesel; the middle layer being glycerin, methanol, water and excess catalyst; and the bottom layer being salts and other solids. This basic method works. However, in order to eliminate the methanol to a level below 1%, which is a requirement for most customers of glycerin, this method is not sufficient.

Many prior patents relating to the purification of glycerin, such as U.S. Pat. Nos. 2,615,924, 2,741,638 and 2,772,207, are aimed at purifying glycerin from high percentages of water, such as those resulting from fermentation and hydrolysis. Whereas, U.S. Pat. No. 2,234,400 describes purification after concentrating the glycerin to a purity of 80% comprising one or more steam distillations followed by treatment with activated carbon or the like to remove color. Even then, the impurities found in glycerin from the biodiesel production process, such as alcohol, are not discussed.

U.S. Pat. No. 4,655,879 describes an approximately 10-step process comprising alkalizing in the presence of air, evaporating in a thin-film evaporator, redistillation of the residue, rectification in a low-pressure-drop column with reboiling in a falling-film evaporator, main product removal as a liquid sidestream, with carbon treatment for color removal.

In the references discussed in the preceding two paragraphs, methanol was not present, or not mentioned, as a constituent in the crude feed.

U.S. Pat. No. 7,126,032 mentions methanol as a constituent of the crude glycerin feed and it also mentions water from the waste stream of biodiesel production. The patent describes neutralizing the glycerin to pH 7. However, the process for purification utilizes different pieces of distillation equipment and the design relies on nitrogen gas. Furthermore, there are more steps involved in the process and the purity of glycerin produced is 99%. In contrast, in the process described in this application, the result is a technical grade glycerin ranging from 80-90% purity.

In summary, a new method of refining glycerin from the biodiesel refining process needs to be developed that takes up a small space and has a cost below $1,000,000. This would allow biodiesel refineries to have a sellable commodity glycerin into a technical market. The following invention solves these issues.

SUMMARY

The present invention may be embodied as a process for purifying glycerin recovered from a fatty acid alkyl ester process, such as the production of biodiesel fuel, as well as an alcohol recovery system. In one aspect of the invention, the process for purifying glycerin recovered from a fatty acid alkyl ester process may be mounted on a skid and/or installed in a small footprint arrangement.

Figure 2:
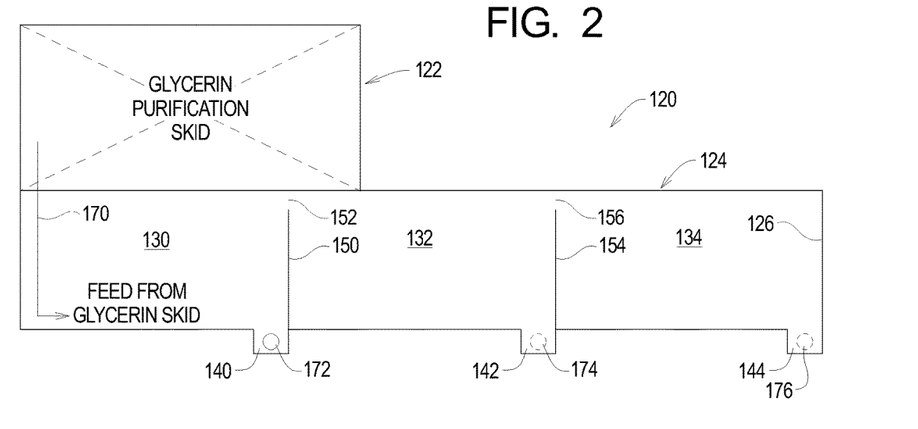
FIG. 2 is a side elevation view of a skid assembly and settling tank that may be used in conjunction with a glycerin purification system such as the first example glycerin purification system of FIG. 1.

According to one embodiment of the invention, a continuous process for purifying glycerin from biodiesel production comprises providing a crude glycerin stream recovered from fatty acid alkyl ester production. The crude glycerin stream comprises glycerin, at least one low molecular weight alcohol, at least one glyceride, at least one fatty acid ester of the alcohol, at least one salt and water. The glycerin stream is heated in a cascading heat exchanger arrangement with the crude glycerin entering from the top in order to reduce the build-up of salts in the heat exchangers. The crude glycerin is pumped in a continuous horizontal flash evaporator. The glycerin is heated to 250-350 degrees F., and the alcohol and water are removed and separated (FIG. 2). The alcohol stream can be reused in the production of fatty acid alkyl esters, used as a boiler fuel to provide heat for the purification process, sold, or otherwise disposed of.

The glycerin stream, which has had the alcohol and water removed and is still hot from the evaporation system, is pumped through the cascading heat exchangers to recover the heat and then the dehydrated glycerin is sent through a three stage continuous settling system where the dehydrated glycerin is separated into three phases. The top phase is richer in oils and fatty acids. The middle phase is rich in glycerin and the bottom phase is rich in settled salts. The result is a purified glycerin of 80 to 98% purity that may be referred to as industrial grade and which is suitable for many industrial uses.

The present invention may thus be embodied as a glycerin recovery system comprising a reboiler and a heat exchanging system. The reboiler heats crude glycerin to separate the crude glycerin into finished glycerin and condensates such that the finished glycerin is in a range of 80-98% purity. The heat exchanging system transfers heat energy in the finished glycerin to the crude glycerin.

The present invention may also be embodied as a glycerin purification system comprising a reboiler and a heat exchanging system. The reboiler heats crude glycerin to separate the crude glycerin into finished glycerin and condensates such that the finished glycerin is in a range of 80-98% purity. The heat exchanging system transfers heat energy in the finished glycerin to the crude glycerin.

The present invention may also be embodied as a method of purifying glycerin comprising the steps of heating crude glycerin to separate the crude glycerin into finished glycerin and condensates such that the finished glycerin is in a range of 80-98% purity and transferring heat energy in the finished glycerin to the crude glycerin.

DETAILED DESCRIPTION

Figure 1:
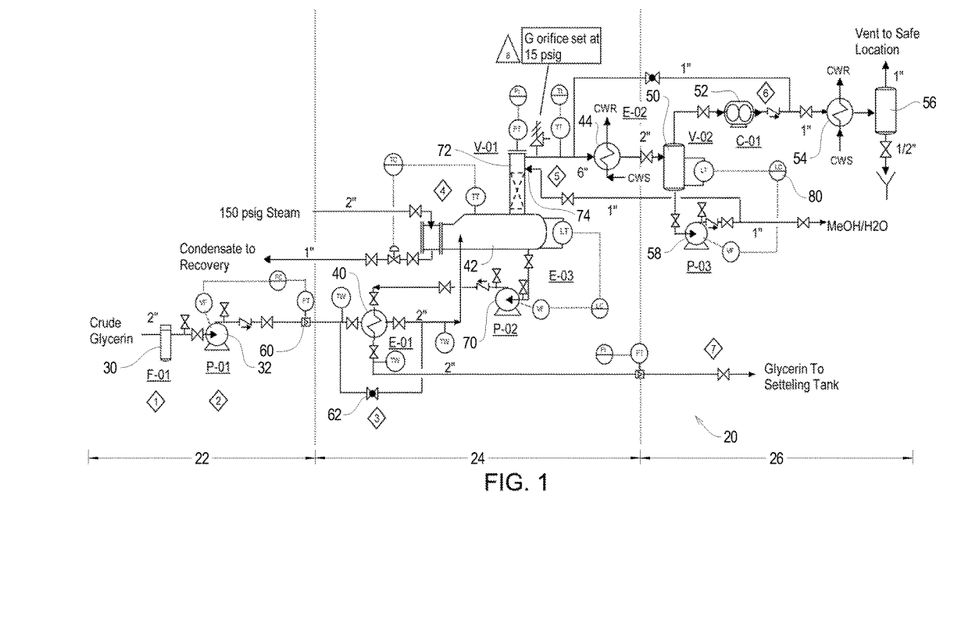
FIG. 1 is a process diagram depicting a first example glycerin purification system of the present invention.

Referring initially to FIG. 1, depicted therein is a first example glycerin purification system 20 constructed in accordance with, and embodying, the principles of the present invention. FIG. 1 illustrates that the first example glycerin purification system 20 comprises an input stage 22, a dehydration stage 24, and a product separation stage 26. The input stage 22 filters the incoming crude glycerin. The dehydration stage 24 dehydrates and removes volatiles from the crude glycerin. The product separation stage 26 separates the volatiles into vapors and salts and recovers at least a portion of any glycerin removed from the dehydration stage along with the volatiles.

More specifically, the example input stage 22 comprises a filter 30 and a pump 32. The pump 32 draws crude glycerin from a source (not shown), through the filter 30, and into the dehydration stage 24. The example dehydration stage 24 comprises a heat exchanger 40, a reboiler 42, and a condenser 44. The product separation stage 26 comprises a first condensate tank 50, a vacuum pump 52, a final condenser 54, a second condensate tank 56, and a reflux pump 58. The operation of the first example glycerin purification system 20 will now be described with reference to FIG. 1 of the drawing.

In the first example glycerin purification system 20, the pump 32 draws crude glycerin through the filter 30 from a source such as a storage vessel (e.g., tank, a railcar) or directly from a biodiesel refinery. When connected directly to a biodiesel refinery, the first example glycerin purification system 20 may operate in a continuous mode as will be apparent from the following discussion.

The example pump 32 is a positive displacement pump that continuously pulls the glycerin from the source into the dehydration stage 24 of the first example glycerin purification system 20. In the first example glycerin purification system 20, the example pump 32 is controlled by a flow controller 60, but the example pump 32 may be controlled by one or both of the flow controller 60 as shown and a level controller on the glycerin reboiler.

Upon entering the dehydration stage 24, the crude glycerin is heated in the example heat exchanger 40 by heat energy in the hot finished glycerin leaving the first example glycerin purification system 20. The example heat exchanger 40 is depicted as a single stage heat exchanger, but multiple heat exchanger stages may be implemented by the example heat exchanger 40 as will be described in further detail below. A bypass valve 62 is arranged to allow the incoming crude glycerin to bypass the heat exchanger 40 if it is not desired or necessary to heat the incoming crude glycerin.

The pre-heated crude glycerin next enters the reboiler 42 of the dehydration stage 24. The example reboiler 42 is a continuous horizontal flash evaporator, but other apparatus for performing the function of the example reboiler 42 as described herein may be used. Accordingly, in the first example glycerin purification system 20, the pre-heated crude glycerin is heated with steam within the reboiler 42 such that a temperature of the crude glycerin is elevated to a desired temperature. In addition to or instead of steam, hot oil and/or electricity may be used to heat the crude glycerin within the reboiler 42. Live steam can also be directly shot into the reboiler to enable steam stripping as a method of distilling the glycerin at a lower temperature.

A pump 70 draws the hot finished glycerin out of the reboiler 42 and through the heat exchanger 40 as described above. After at least a portion of the heat energy is extracted from the finished glycerin by the heat exchanger 40, the finished glycerin may be direct to a storage tank such as a settling tank as will be described in further detail below. A decanting three-product centrifuge could be used in addition or as an alternative to the settling tanks. While a decanting three-product centrifuge takes up less space than one or more settling tanks as described below, the settling tanks provide integral storage capacity not provided with a centrifuge. Additional storage tanks would be required if a decanting three-product centrifuge is used in place of the settling tanks as described below.

If removing water and methanol is the prime objective of the first example glycerin purification system 20, the temperature of the crude glycerin is raised within the reboiler to a desired temperature within a range of 300-380 degrees F. If the goal is to distill the glycerin, the temperature is typically raised to a range of 500-600 degrees F.

The product being distilled out of the crude glycerin by the dehydration stage 24 goes up a packed column portion 72 of the reboiler 42. The column portion 72 includes spray nozzles 74 that spray a reflux material into the column portion 72 to increase the purity of the final product. The orifice sizes of the spray nozzles 74 may be changed depending on a flow rate of vapor flowing up the column portion 72. The vapors exiting the column portion 72 of the reboiler 42 next go through the condenser 44. The example condenser 44 is sized to provide a vacuum from the condensing of the vapors such that the vacuum draws the vapors out of the column portion 72.

The condensed product goes into the first holding tank 50. A level controller 80 detects the level of the condensed product in the first holding tank and, as the first holding tank 50 fills, the reflux pump 58 forces some of the condensed product back into the column portion 72 as a reflux and some of the condensed product goes to a condensed product holding tank (not shown).

Any vapors that escape the first holding tank 50 are drawn by the vacuum pump 52 out of the holding tank 50 and are condensed by the final condenser 54. The remaining condensed product is stored by the second holding tank 56.

As described above, the final product (finished glycerin) from the reboiler 42 that has been dehydrated or is not able to be distilled is utilized for heat recovery in by the heat exchanger 40 and then pumped out to storage or, as will be described below, to an optional three stage settling tank.

Figure 3:
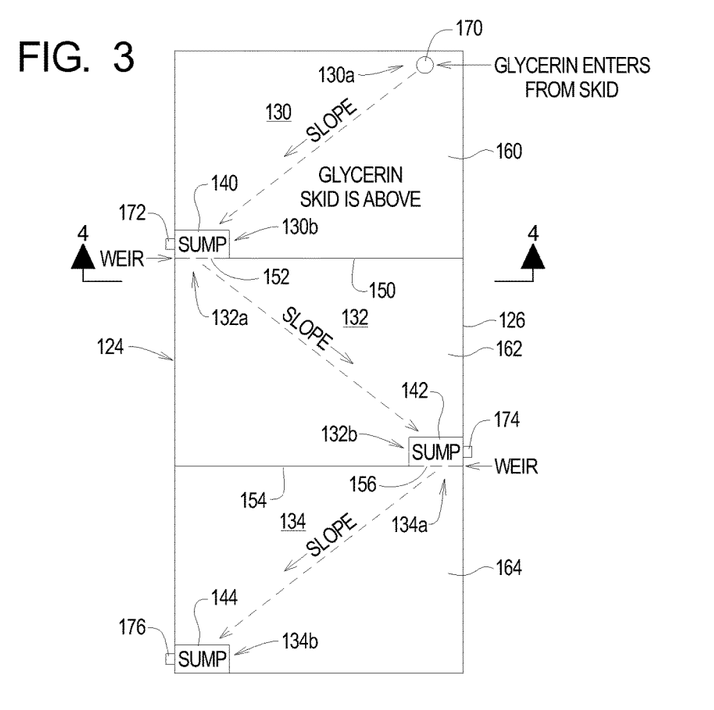
FIG. 3 is a top plan view illustrating an example weir system that may be used by the settling tank of FIG. 2.
Figure 4:
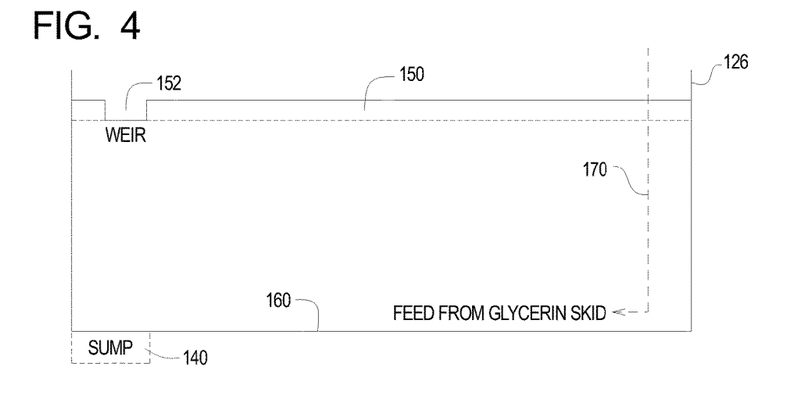
FIG. 4 is a section view taken along lines 4-4 in FIG. 3 illustrating the weir system of FIG. 3.

Turning now to FIGS. 2-4 of the drawing, depicted therein is a glycerin recovery system 120 comprising a glycerin purification system 122 and a three stage settling system 124. The glycerin purification system 122 may be any of the example glycerin purification systems described in this application, such as the first example glycerin purification system 20 described above or the example glycerin purification system 220 described below. The glycerin recovery system 120 is of particular significance when the glycerin purification system 122 is of a compact design that may be mounted on a skid as will be described in further detail below, and the example glycerin purification system 122 is optimized for such a compact design. The construction and operation of the glycerin purification system will not be described with reference to FIGS. 2-4 beyond that extent necessary for a complete understanding of the example glycerin recovery system 120.

As shown in FIG. 2, the example glycerin purification system 122 is skid mounted and is sized and dimensioned to be located above the settling system 124. FIGS. 2 and 3 illustrate that the example settling system 124 comprises a settling tank structure 126 defining first settling tank compartment 130, a second settling tank compartment 132, and a third settling tank compartment 134. FIG. 2 also shows that the example skid-mounted glycerin purification system 122 is arranged above the first compartment 130 and a portion of the second compartment 132.

The first compartment 130 defines a first sump 140, the second compartment 132 defines a second sump 142, and the third compartment 134 defines a third sump 144. The settling tank structure 126 further comprises a first weir wall 150 defining a first weir 152 is arranged between the first and second compartments 130 and 132 and a second weir wall 154 defining a second weir 156 is arranged between the second and third compartments 132 and 134. First, second, and third bottom wall portions 160, 162, and 164 of the tank structure 126 are arranged under the first, second, and third compartments 130, 132, and 134, respectively.

As shown in FIG. 3, the first compartment 130 defines a first opposing portion 130a and a second opposing portion 130b. Similarly, the second compartment 132 defines a first opposing portion 132a and a second opposing portion 132b, and the third compartment 134 defines a first opposing portion 134a and a second opposing portion 134b. A feed pipe 170 extends from the example glycerin purification system 122 to the first opposing portion 130a of the first compartment 132. First, second, and third exit pipes 172, 174, and 176 are connected to the first, second, and third sumps 140, 142, and 144 as shown in FIGS. 2 and 3.

FIG. 3 further illustrates that example the tank structure 126 is rectangular in cross-section and that the weir walls 150 and 154 are configured such that the compartments 130, 132, and 134 are similarly rectangular in cross-section. The first opposing portions 130a, 132a, and 134a are in opposite corners of the compartments 130, 132, and 134 from the respective second opposing portion 130b, 132b, and 134b. Further, the second opposing portion 130b of the first compartment 130 is adjacent to the first opposing portion 132a of the second compartment 132, while the second opposing portion 132b of the second compartment 132 is adjacent to the first opposing portion 134a of the third compartment 134.

Further, FIGS. 2-4 illustrate that the first weir 152 is located at the top of the first weir wall 150 above the second opposing portion 130b of the first compartment 130 and the first opposing portion 132a of the second compartment 132. The second weir 156 is located at the top of the second weir wall 154 above the second opposing portion 132b of the second compartment 132 and the first opposing portion 134a of the third compartment 134.

FIG. 3 further illustrates that the bottom walls 160, 162, and 164 of the tank structure 26 are slanted. In particular, the first bottom wall 160 is sloped from the first opposing portion 130a to the second opposing portion 130b, the second bottom wall 162 is sloped from the first opposing portion 132a to the second opposing portion 132b, and the third bottom wall 164 is sloped from the first opposing portion 134a to the second opposing portion 134b. The sloped bottom walls 160, 162, and 164 thus form a zig zag pattern that extends from the feed pipe 170 to the first sump 140 and first weir 152, from the first sump 140 to the second sump 142 and the second weir 154, and from the second sump 142 to the third sump 144.

The feed pipe 170 conveys finished glycerin product from the example glycerin purification system 122 to the first opposing portion 130a of the first compartment 130. The finished glycerin product entering the settling system 124 will thus initially fill up the first compartment 130. When the finished glycerin product in the first compartment 130 reaches the level of the first weir 152, the finished glycerin product will spill over into the second compartment 132. The finished glycerin product within the settling system 124 will thus next fill up the second compartment 132. When the finished glycerin product in the second compartment 132 reaches the level of the second weir 156, the finished glycerin product will spill over into the third compartment 134. The finished glycerin product within the settling system 124 will thus next fill up the third compartment 134.

The glycerin recovery system 120 thus operates generally as follows. Finished glycerin that has been purified from the skid-mounted glycerin purification system 122 is pumped or falls from gravity through the feed pipe 170 to first opposing portion 130a near the bottom wall portion 160 below the first compartment 130 of the continuous settling tank structure 126.

The glycerin within the first compartment 130 flows along the sloped bottom wall 160 towards the first weir 152 between the first and second settling compartments 130 and 132. As the glycerin rises up the first weir wall 150 towards the first weir 152, salt settles out of the glycerin within the first compartment 130 and falls to the bottom of the compartment 130. Salts thus concentrate at the bottom of the first compartment 130, and collect within the first sump 140, and thus can be pumped out of the settling system 124 through first sump 140 and into the first outlet pipe 172 for storage in a first (salts) storage tank (not shown).

The glycerin that has flowed through the first weir 152 into the second compartment 132 of the settling tank structure 126 flows toward the second weir wall 154 and the second weir 156. The glycerin settles to the bottom of the second compartment 132 and an oil and fatty acid layer rises such that the oils and fatty acids flow over the top of the second weir wall 154 through the second weir 156. Glycerin thus concentrates at the bottom of the second compartment 132, and collects within the second sump 142, and can thus be pumped out of the settling system 124 through second sump 142 and into the second outlet pipe 174 for storage in a second (glycerin) storage tank (not shown).

Similarly, oils and fatty acids that flow through the second weir 156 concentrate in the third compartment 134 of the settling tank structure 126 and can be pumped out of the third sump 144 and into suitable storage tanks (not shown).

Accordingly, after glycerin is fed into the bottom of the first compartment 130, the arrangement of the slopes on the bottom walls 160, 162, and 164 and the first and second weirs 152 and 156 on the first and second weir walls 150 and 154 is designed so that the glycerin flows at an angle from the point it is fed into each of the settling tank compartments 130, 132, and 134. This flow path maximizes the retention time in each settling tank, allowing for more separation of salts, glycerin, and/or oils and fatty acids. As described above, the main separation of salts occurs in the first setting tank compartment 130. Most of the glycerin concentrates and settles out from the lighter oils and fatty acids in the second settling tank compartment 132. Most of the oils and fatty acids concentrate in the third settling tank compartment 134.

FIG. 4 illustrates that the first and second weirs 152 and 154 are square holes or notches in the top of the respective weir walls 150 and 154 separating the first and second settling tank compartments 130 and 132 and the second and third settling tank compartments 132 and 134. The size of the weir controls the flow rate of the continuous settling tank. The sumps 140, 142, and 144 form the lowest points in the settling tank compartments 130, 132, and 134 and thus facilitate the removal of product from the settling tank compartments 130, 132, and 134.

Figure 5:
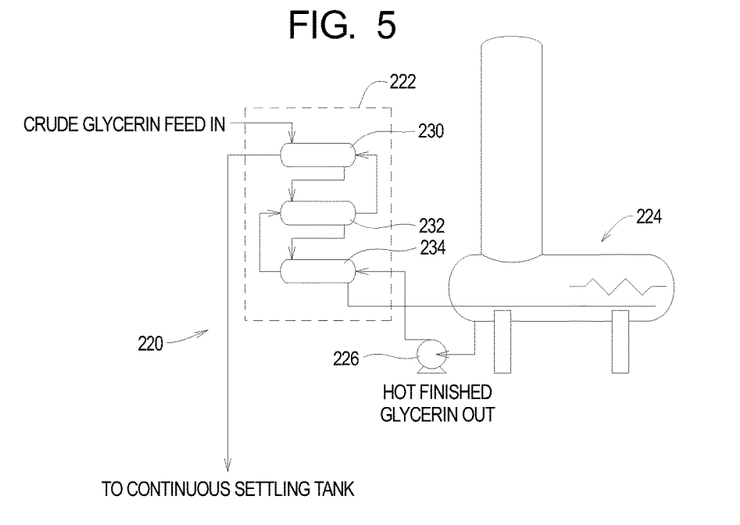
FIG. 5 is a side elevation view of a third example glycerin purification system of the present invention employing a cascading heating system.

Turning now to FIG. 5 of the drawing, depicted at 220 therein is a third example glycerin purification system constructed in accordance with, and embodying, the principles of the present invention. The third example glycerin purification system 220 comprises a heat exchanger system 222, a reboiler 224, and a pump 226.

The heat exchanger system 222, reboiler 224, and pump 226 will typically be embodied as part of a larger glycerin purification system such as the first example glycerin purification system 20 described above. In particular, the heat exchanger system 222 and reboiler 224 may be substituted for the heat exchanger 40, reboiler 42, and pump 70 of the first example glycerin purification system 20. The construction and operation of the third example glycerin purification system 220 will thus be described herein in the context of the description of the first example glycerin purification system 20 as set forth above and in FIG. 1.

The example heat exchanger system 222 comprises a first heat exchanger 230, a second heat exchanger 232, and a third heat exchanger 234. As shown in FIG. 5, the first heat exchanger 230 is located above the second heat exchanger 232 and the second heat exchanger 232 is located above the third heat exchanger 234. The crude glycerin is fed in series initially into the first heat exchanger 230, then to the second heat exchanger 232, and then to the third heat exchanger 234. In the third example glycerin purification system 220, the hot finished glycerin from the reboiler 224 is fed in series first into the third heat exchanger 234, then into the second heat exchanger 232, and then into the first heat exchanger 230. In some embodiments of the invention, it may be possible to feed the hot finished glycerin from the reboiler 224 in series first into the first heat exchanger 230, then into the second heat exchanger 232, and then into the third heat exchanger 234. In other embodiments of the invention, the hot finished glycerin may be fed in parallel to the first, second, and third heat exchangers 230, 232, and 234.

In any embodiment, the hot glycerin from the reboiler 224 is continuously pumped out and into the vertically stacked heat exchangers 230, 232, and 234. In the example heat exchanger system 222, the hot glycerin first goes through the lowest (third) heat exchanger 234, then through the next highest or intermediate (second) heat exchanger 232, then to the top (first) heat exchanger 230. The hot glycerin that has passed through the heat exchangers 230, 232, and 234 then goes to storage (not shown) for further processing such as by the settling tank system 124 described above.

At the same time, cold crude glycerin is pumped into the top of the first heat exchanger 230. The crude glycerin goes through the first heat exchanger 230 with the flow of gravity and then into the second heat exchanger 232 and then into the third heat exchanger 234. The importance of flowing with gravity is that, as the glycerin heats up, salts begin to fall out. So long as the flow is with gravity, the salts do not collect in the heat exchangers 230, 232, and 234 and thus plug or otherwise obstruct flow of crude glycerin through the heat exchanger system 222.

As with the first example glycerin purification system 20 described above, after the crude glycerin is preheated by passing through the heat exchanger system 222, the preheated glycerin goes into the reboiler 224, which may be a horizontal flash evaporator as generally described above.

Figure 6:
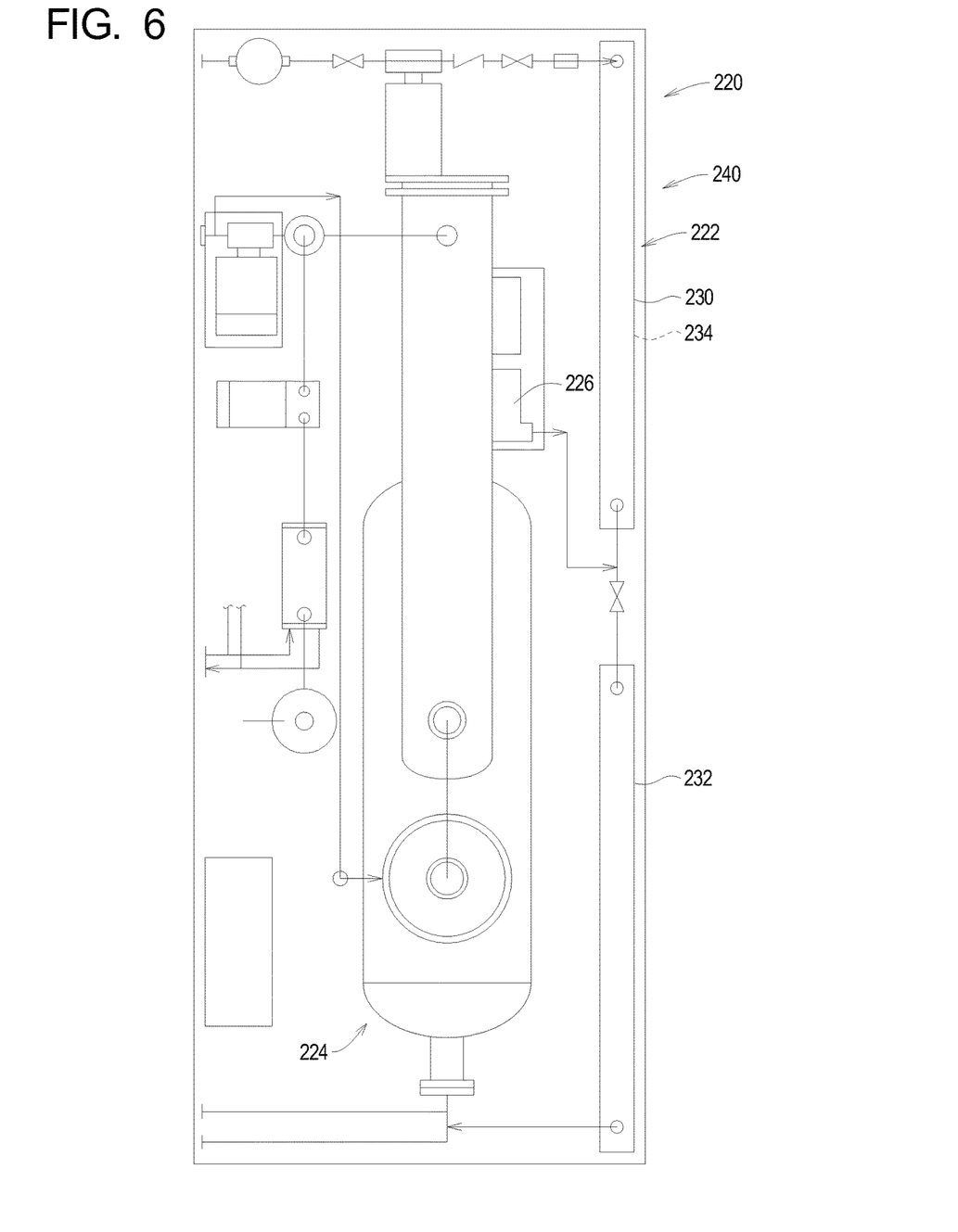
FIG. 6 is a top plan view of the second example glycerin purification system as mounted on a skid assembly such as the skid assembly depicted in FIG. 2.

FIG. 6 is a top plan view of a skid structure 240 on which the glycerin purification system 220 may be mounted. FIG. 6 illustrates that the reboiler 224 is substantially centrally located on the example skid structure 240 The heat exchanger system 222 is mounted along one edge of the skid structure 240 with the first heat exchanger 230 stacked directly above the third heat exchanger 234 and the second heat exchanger 232 laterally spaced from the first and second heat exchangers 230 and 234. As shown and described with reference to FIG. 5, however, when the glycerin purification system 220 is mounted on the example skid structure 240, the first heat exchanger 230 is located above the second heat exchanger 232 and the second heat exchanger 232 is located above the third heat exchanger 234 with reference to the downward flow of cold crude glycerin and upward flow of hot finished glycerin through the heat exchanger system 222 as described above with reference to FIG. 5.

FIG. 6 thus depicts a configuration of the third example glycerin purification system 220 optimized for mounting on the skid structure 240. Again, the example glycerin purification system 220 is capable of recovering the alcohol and water from the glycerin. The glycerin that is run through the purification system will be of a technical grade within a range of from 80 to 98% purity.

Further, the process implemented by the third example glycerin purification system 220 is designed such that crude glycerin from a source such as a tank, a railcar, or a refinery is continuously processed as generally described above.

Alternatively, high pressure steam can be applied to the crude glycerin in the reboiler to undergo steam stripping. The steam stripping process will carry the glycerin through the column and condenser. This will result in a water white wet glycerin that can be run through the still in a dehydration mode resulting in a water white glycerin that as high as 99% pure but typically in the range of about 85-98% purity.

Turning now to FIGS. 8-12 of the drawing, depicted therein is an example reboiler 320 having a tank structure 322. The example reboiler 320 used as the reboiler 42 or reboiler 224 as described above. The example tank structure 322 defines a main tank portion 330 and a column portion 332. The main tank portion 330 defines a cylindrical central portion 334 and first and second spherical end caps 336 and 338. The main tank portion 330 defines a main chamber 340. Secured to an interior surface 342 defined by the main tank portion 330 of the tank structure 322 are first, second, third, fourth, and fifth baffle plates 350, 352, 354, 356, and 358. Supported by the main portion 330 of the tank structure 322 are a steam inlet 360, a crude glycerin inlet 362, and a finished glycerin outlet 364. A condensed product outlet 366 is supported by the column portion 332.

Figure 7:
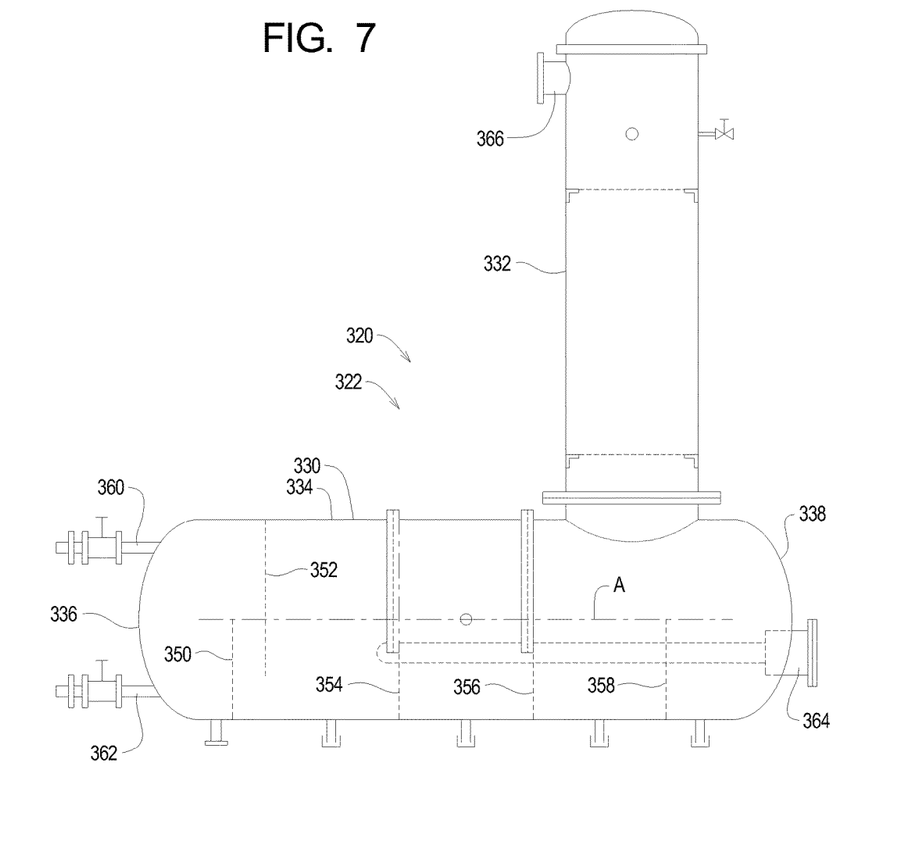
FIG. 7 is a side elevation view of a first example reboiler that may be used as part of the first and second example glycerin purification systems as described above.
Figure 8:
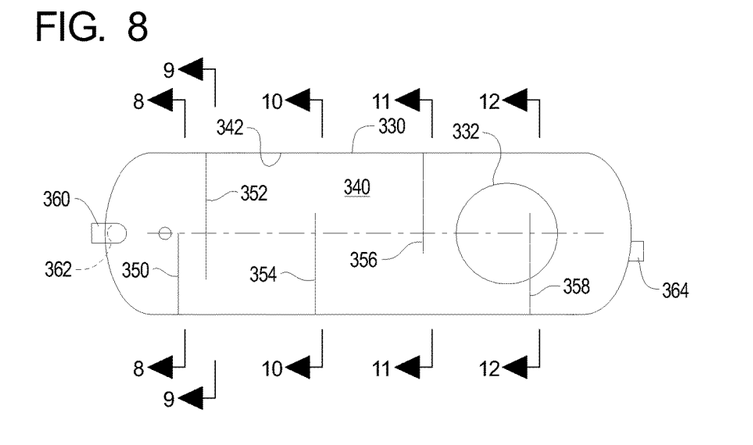
FIG. 8 is a top plan view depicting details of a first example baffle system of the first example reboiler of FIG. 7.

The baffle plates 350-358 are sized, dimensioned, shaped, and located to improve the operation of the reboiler 320. In particular, as shown in FIGS. 7-12, the steam inlet 360 extends from the first spherical end cap 336 above a centerline A of the main tank portion 330 and the crude glycerin inlet 362 extends from the first spherical end cap 336 below the centerline A. FIGS. 7 and 8 illustrate that the finished glycerin outlet 364 extends from the second spherical end cap 338 below the centerline A.

Figure 9:
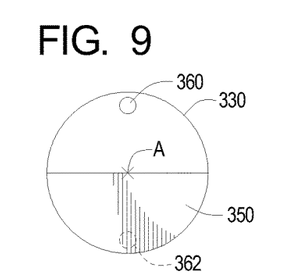
FIGS. 9-13 are section views taken along lines 9-9, 10-10, 11-11, 12-12, and 13-13 in FIG. 8 and illustrate details of example baffle plates that may be used as part of the first example baffle system.
Figure 10:
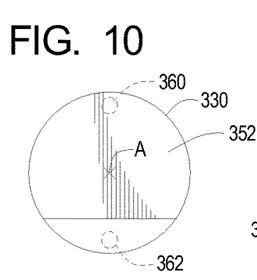
Figure 11:
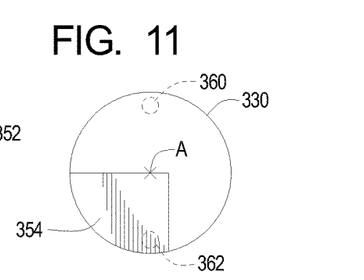
Figure 12:
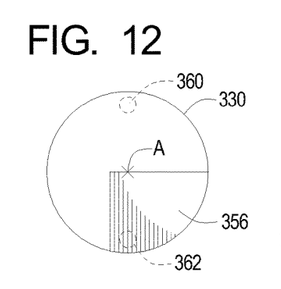
Figure 13:
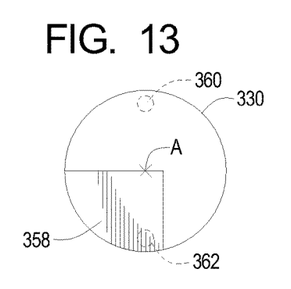

Further, FIGS. 9-13 illustrate that the baffle plates 350-358 are arranged to restrict flow of fluid from the first spherical end cap 336 to the second spherical end cap 338. In particular, FIG. 9 shows that the first baffle plate 350 extends up from the tank interior surface 342 to the centerline A such that approximately the bottom 50% of the main tank portion 330 is restricted. FIG. 10 illustrates that the second baffle plate 352 extends down from the tank interior surface 342 to below the centerline A such that approximately the upper 85% of the main tank portion 330 is restricted. FIG. 11 shows that the third baffle plate 354 extends up from the tank interior surface 342 to the centerline A but only along a first radial portion of the interior surface 342 such that approximately 35% of the bottom of the main tank portion 330 is restricted. FIG. 12 shows that, like the third baffle plate 354, the fourth baffle plate 356 extends up from the tank interior surface 342 to the centerline A but only along a second radial portion of the interior surface 342 such that approximately 35% of the bottom of the main tank portion 330 is restricted. A comparison of FIGS. 11 and 12 shows that the second portion radial portion is offset from the first radial portion. FIG. 13 shows that the fifth baffle plate 354 extends up from the tank interior surface 342 to the centerline A but only along a third radial portion of the interior surface 342 such that approximately 35% of the bottom of the main tank portion 330 is restricted. A comparison of FIGS. 11, 12, and 13 shows that the third radial portion is aligned with the first radial portion and offset from the second radial portion.

With this arrangement of baffle plates 350-358, glycerin flowing from the crude glycerin inlet 362 to the finished glycerin outlet 364 must travel along a serpentine flow path that first causes the glycerin to flow up and over the first baffle plate 350, down and under the second baffle plate 352, over and to a first side of the third baffle plate 354, over and to a second side of the fourth baffle plate 356, and over and to the first side of the fifth baffle plate 358. This flow path optimizes the processing of the glycerin flowing through the example reboiler 320.

What is claimed is:

1. A glycerin purifying system comprising:
   a reboiler for heating crude glycerin to separate the crude glycerin into finished glycerin and condensates; and
   a heat exchanging system for transferring heat energy in the finished glycerin to the crude glycerin;
   a settling tank system arranged below the heat exchanger, the settling tank system comprising first, second, and third settling tank compartments separated by first and second weir walls, where
   the first and second weir walls define first and second weirs, respectively,
   the first, second, and third settling tank compartments define first, second, and third sumps, respectively,
   the first sump is located below the first weir, and
   the second sump is located below the second weir; wherein
   fluid flows from the first settling tank compartment to the second settling tank compartment through the first weir and from the second settling tank compartment to the third settling tank compartment through the second weir.

2. A glycerin purifying system as recited in claim 1, in which:
   the heat exchanging system comprises at least one heat exchanger; and
   the crude glycerin is introduced into the at least one heat exchanger such that the crude glycerin flows down through the at least one heat exchanger.

3. A glycerin purifying system as recited in claim 2, in which the finished glycerin is introduced into the at least one heat exchanger such that the finished glycerin flows up through the at least one heat exchanger.

4. A glycerin purifying system as recited in claim 1, in which:
   the heat exchanging system comprises a plurality of vertically spaced heat exchangers; and
   the crude glycerin is caused to flow through the plurality of vertically spaced heat exchangers such that the crude glycerin first flows through an upper one of the plurality of vertically spaced heat exchangers and then through a lower one of the plurality of vertically spaced heat exchangers.

5. A glycerin purifying system as recited in claim 4, in which the finished glycerin is caused to flow through the plurality of vertically spaced heat exchangers such that the finished glycerin first flows through a lower one of the plurality of vertically spaced heat exchangers and then through an upper one of the plurality of vertically spaced heat exchangers.

6. A glycerin purifying system as recited in claim 1, in which:
the heat exchanging system comprises first, second, and third heat exchangers;
the first heat exchanger is arranged above the second heat exchanger and the second heat exchanger is arranged above the third heat exchanger; and
the crude glycerin is caused to flow through in series through the first heat exchanger, then through the second heat exchanger, then through the third heat exchanger.

7. A glycerin purifying system as recited in claim 6, in which the finished glycerin is caused to flow in series through the third heat exchanger, then through the second heat exchanger, then through the first heat exchanger.

8. A glycerin purifying system as recited in claim 1, in which:
the heat exchanging system comprises at least one heat exchanger; and
the crude glycerin is introduced into the at least one heat exchanger such that gravity carries salts that precipitate from the crude glycerin down through the at least one heat exchanger as the crude glycerin flows through the at least one heat exchanger.

9. A glycerin purifying system as recited in claim 8, in which the finished glycerin is introduced into the at least one heat exchanger such that the finished glycerin flows up through the at least one heat exchanger.

10. A glycerin purifying system as recited in claim 1, in which the reboiler and the heat exchanger are mounted on a skid.

11. A glycerin purifying system as recited in claim 1, in which bottom walls of the settling tank structure are slanted towards the sumps.

12. A glycerin purifying system as recited in claim 1, in which the reboiler comprises a plurality of baffles that cause glycerin to flow through the reboiler along a flow path that directs the glycerin up, down, to a first side, and to a second side.

13. A method of purifying glycerin comprising the steps of:
heating crude glycerin to separate the crude glycerin into finished glycerin and condensates; and
transferring heat energy in the finished glycerin to the crude glycerin;
providing a settling tank system comprising first, second, and third settling tank compartments separated by first and second weir walls, where
the first and second weir walls define first and second weirs, respectively,
the first, second, and third settling tank compartments define first, second, and third sumps, respectively,
the first sump is located below the first weir,
the second sump is located below the second weir, and
arranging the settling tank system below the heat exchanger;
allowing fluid to flow from the first settling tank compartment to the second settling tank compartment through the first weir and from the second settling tank compartment to the third settling tank compartment through the second weir.

14. A method as recited in claim 13, in which:
the step of transferring heat energy in the finished glycerin to the crude glycerin comprises the step of providing a plurality of heat exchangers;
arranging a first one of the plurality of heat exchangers above a second one of the plurality of heat exchangers; and
causing the crude glycerin to flow through the plurality of vertically spaced heat exchangers such that the crude glycerin first flows through the first one of the plurality of vertically spaced heat exchangers and then through the second one of the plurality of vertically spaced heat exchangers.

15. A method as recited in claim 13, in which the step of heating the crude glycerin comprises the step of causing glycerin to flow through a reboiler along a flow path that directs the glycerin up, down, to a first side, and to a second side.

* * * * *